United States Patent [19]

Furuya

[11] Patent Number: 4,882,031

[45] Date of Patent: Nov. 21, 1989

[54] GAS SENSOR

[75] Inventor: Nagakazu Furuya, No. 4-3-31, Ohte 2-chome, Kofu-shi, Yamanashi, Japan

[73] Assignees: Nagakazu Furuya; Tanaka Kikinzoku Kogyo K.K., both of Japan

[21] Appl. No.: 288,304

[22] Filed: Dec. 22, 1988

[30] Foreign Application Priority Data

Dec. 22, 1987 [JP] Japan .................. 62-324285

[51] Int. Cl.$^4$ ............................. G01N 27/46
[52] U.S. Cl. .................... 204/415; 204/291; 204/294
[58] Field of Search ............ 204/1, 415, 291, 294

[56] References Cited

U.S. PATENT DOCUMENTS

| 3,239,444 | 3/1966 | Heldenbrand | 204/415 |
| 3,510,420 | 5/1970 | Mills | 204/415 |
| 3,718,563 | 2/1973 | Krull et al. | 204/415 |
| 4,479,865 | 10/1984 | Beder et al. | 204/415 |
| 4,587,003 | 5/1986 | Tantram et al. | 204/415 |

Primary Examiner—T. Tung

Attorney, Agent, or Firm—Klauber & Jackson

[57] ABSTRACT

Disclosed herein is a gas sensor comprising a membrane for gas sensing which comprises a selective gas permeable membrane and a reaction layer attached thereto; and a counter electrode separated from the reaction layer of the membrane across an electrolyte; the reaction layer having the function of an electrode and comprising fine hydrophilic portions and fine hydrophobic portions.

The specific gas in mixed gases having permeated the selective gas permeable membrane is immediately dissolved in the electrolyte having penetrated into the reaction layer and is ionized and the ion in the electrolyte moves to the counter electrode closely positioned to the reaction layer so that the specific gas concentration can be detected by means of the voltage difference or the like.

Since, therefore, in the sensor of the present invention, the specific gas easily reaches the counter electrode, the response time can be greatly decreased and the scale of the apparatus can be easily made smaller because extra equipment and space are not required.

3 Claims, 2 Drawing Sheets

GAS SENSOR

BACKGROUND OF INVENTION

The present invention relates to a gas sensor which is superior in response characteristic and is capable of being small-sized.

A sensor for various gases such as oxygen, hydrogen, hydrogen peroxide, ammonia, carbon dioxide and the like has been heretofore employed in a broad range of technical fields. An ordinary sensor separates a particular gas component from mixed gases to detect the concentration of the particular gas by means of a detecting apparatus. A gas permeable membrane which selectively lets the particular gas pass through is employed for the separation of the mixed gases, and the detection of the particular gas in the mixed gases is carried out by, for example, measuring electric energy after the concentration of the separated gas is converted into the electric energy. FIG. 1 is a vertical cross-sectional view showing an example of a conventional gas detecting sensor. The sensor consists of an upper curved permeable membrane A which lets a specific gas pass through; a platinum electrode E which consists of a curved portion B being substantially the same shape as the permeable membrane A, a horizontal portion C inwardly extending from the base portion of the curved portion B and a cylindrical portion D connected with the inner edge of the horizontal portion C; an insulated portion F disposed on the outer surface of the horizontal portion C and the cylindrical portion D of the platinum electrode E; and a counter electrode G surrounding the lower portion of the insulated portion F. An electrolyte H is filled in the space between the permeable electrode A and the curved portion B and in the space around the insulated portion F.

When the conventional sensor having the thus mentioned construction is employed, mixed gases are provided to the permeable membrane A of the sensor from the upper space as shown by the arrows. A specific component in the mixed gases, for example, hydrogen selectively permeates the permeable membrane A to be dissolved in the electrolyte H so that the dissolved hydrogen reaches the curved portion B of the platinum electrode E on which the hydrogen is ionized to a hydrogen ion. The ion reaches the counter electrode G by the movement of the electrolyte H, and the hydrogen concentration in the mixed gases is detected by measuring the voltage generated between the platinum electrode E and the counter electrode G. The sensor of this type is called a voltage type. On the other hand, a current type is also known in which oxidation or reduction of the detected gas is positively carried out on the platinum electrode and the detected gas concentration is determined by measuring the current generated during the oxidation or reduction.

Since, however, the moving speed of the specific gas in the electrolyte H between the permeable membrane A and the curved portion B is quite slow when either process is employed, a relatively long period of time is required before the gas is detected. When the membrane A and the curved portion B are brought closer in order to shorten the time required, the resistance against the movement of the electrolyte H from the space therebetween to the counter electrode G increases. In any case, the sensor has the disadvantage of being inferior in the response characteristic.

Further, conventional sensors including one shown in the attached drawing are generally large so that a smaller-sized sensor is demanded to meet the requirement of the decrease of the installation area.

SUMMARY OF INVENTION

An object of the present invention is to provide a gas sensor overcoming the above-mentioned disadvantages of the conventional sensor.

Another object of the invention is to provide a gas sensor which is superior in the response characteristic.

A further object of the invention is to provide a small-sized gas sensor.

The present invention is a gas sensor comprising a membrane for gas sensing which comprises a selective gas permeable membrane and a reaction layer attached thereto; and a counter electrode separated from the reaction layer of the membrane across an electrolyte; the reaction layer having the function of an electrode and comprising fine hydrophilic portions and fine hydrophobic portions.

DETAILED DESCRIPTION OF INVENTION

Figure 1:
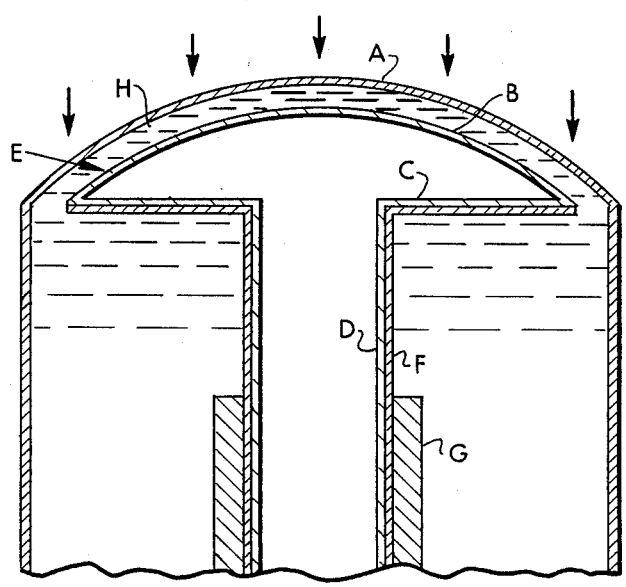
FIG. 1 is a partially vertical section showing an example of a conventional gas sensor.
Figure 2:
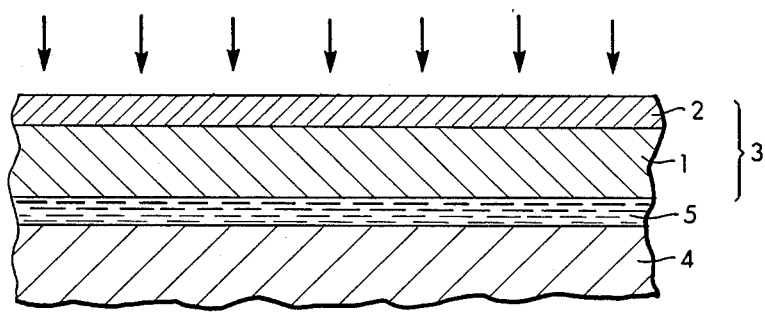
FIG. 2 is a schematic partially vertical section showing one embodiment of a gas sensor according to the invention.

A sensor according to the present invention is employed for the detection of a specific gas in mixed gases, for example, the detection of an impurity gas in a commercially available gas. The kind of gases the subject of the invention is not particularly restricted, and the present invention can be applied to the detection of each of a large number of gases such as oxygen, hydrogen, hydrogen peroxide, ammonia, carbonic acid gas or the like.

A selective gas permeable membrane is a membrane for separating a specific gas to be detected from mixed gases. Although the selective gas permeable membrane may consist of a main membrane for gas separation, it may also be a composite membrane which comprises the main membrane and an auxiliary membrane attached thereto for elevate strength and electro-conductivity. In this case, the main membrane is located in the mixed gas side, and the auxiliary membrane is located in a reaction layer side which will be described below. Any conventional membrane, especially a thin membrane made of an organic polymer, can be employed as the main membrane, and it is of course properly selected depending on the mixed gases employed and the specific gas detected. Neofron (trade name of Daikin Kogyo K.K.) can be employed, for example, to detect $O_2$ gas from the mixed gases consisting of the $O_2$ gas and $N_2$ gas. The auxiliary membrane is preferably made of hydrophobic material similar to that of the hydrophobic portion of a reaction layer below mentioned. Moreover, it is preferably porous not for preventing the movement of the specific gas.

The reaction layer attached to the selective gas permeable membrane (the auxiliary membrane side in case of the composite membrane) comprises fine hydrophilic portions and hydrophobic portions. The hydrophilic portions of the reaction layer comprise, for example, platinum, hydrophilic carbon black, polytetrafluoroethylene (hereinafter referred to as PTFE) and the like, and the hydrophobic portions comprise hydrophobic carbon black, PTFE and the like. In order to prepare the reaction layer, for example, after fine particles are mixed and agitated, the agitated particles can be pressure-molded by hot pressing and the like. Although the platinum particles are desirably buried in the reaction layer as electrode material because the reaction layer also plays the role corresponding to that of an electrode close to the selective gas permeable membrane of a conventional sensor, the particles are not indispensable because the carbon black or the like also has the electrode catalyst function.

A counter electrode to the reaction layer may be one made of any material, but a conventional electrode such as a silver electrode and the like employed in a conventional sensor is preferably employed.

When the sensor having the thus mentioned constitution is employed for the detection of a specific gas in mixed gases, only the specific gas in the mixed gases permeates the selective gas permeable membrane to reach the reaction layer and penetrates into the hydrophobic portions thereof. On the other hand, an electrolyte penetrates into the hydrophobic portions of the reaction layer. Therefore, the specific gas is easily dissolved in the electrolyte at the interface between the hydrophilic portions and the hydrophobic portions of the reaction layer, and is ionized. The ion in the electrolyte moves to the counter electrode close to the reaction layer as it is so that the voltage difference is generated between the counter electrode and the reaction layer. The specific gas having reached the reaction layer and therefore the specific gas concentration in the mixed gases can be detected by detecting the voltage difference by means of an appropriate means.

In the conventional sensor, the specific gas in the gas state moves in the electrolyte H between the permeable membrane A and the curved portion B (gas movement in liquid produces extreme resistance), and the detection can be performed only after the electrolyte H dissolving the ion moves through narrow space to reach the counter electrode G side so that naturally the response speed remarkably decreases. Since, on the other hand, the specific gas having permeated the selective gas permeable membrane in the present invention is dissolved in the electrolyte in the reaction layer which is in contact with the selective permeable membrane to be ionized and the electrolyte dissolving the ion can easily reach the adjacent counter electrode, the response time can be greatly decreased and the scale of the apparatus can be easily made smaller because extra equipment and space are not required.

The invention will now be illustrated by an Example which, however, is to be considered a merely exemplary of practice of the invention, and not as delimitive thereof.

EXAMPLE

After hydrophilic carbon black having an average particle diameter of 420 Å and supporting 10% of platinum particles having an average particle diameter of 50 Å, PTFE particles having an average particle diameter of 0.3μ and hydrophobic carbon black having an average particle diameter of 420 Å were mixed in the proportion of 4:3:3, the mixture was hot-pressed at the pressure of 200 kg/cm$^2$ and at 320° C. to prepare a reaction layer 1 having a thickness of about 0.1 mm. Then, Neofron membrane having a thickness of 25μ of Daikin Kogyo K.K. was employed as a selective gas permeable membrane so that the both were put together at the pressure of 100 kg/cm$^2$ and 300° C. to prepare a sensor membrane 3.

Figure 3:
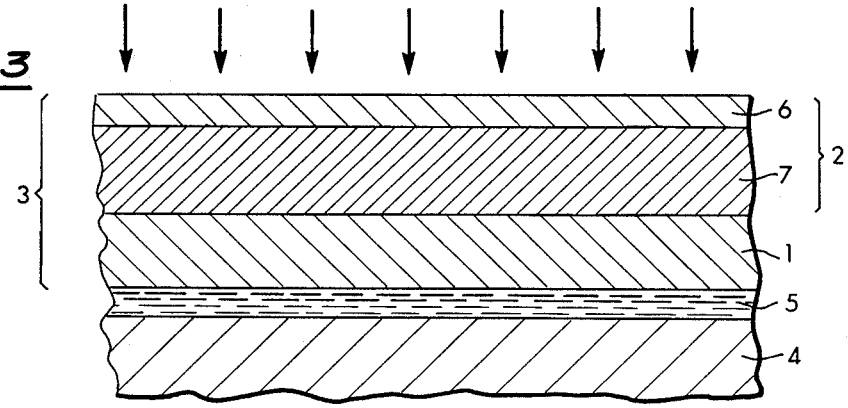
FIG. 3 is a schematic partially vertical section showing another embodiment.

A silver electrode 4 was established as a counter electrode near the sensor membrane 3 and an electrolyte 5 was filled between the reaction layer 1 and the silver electrode 4 to form a gas sensor. When a nitrogen gas containing 100 ppm of a hydrogen gas previously prepared was supplied to the selective gas permeable membrane 2 side of the sensor so that the hydrogen gas concentration was detected by means of the voltage difference generated, the existence of 100 ppm of the hydrogen gas was indicated at the detection side after 2.6 seconds. The selective gas permeable membrane 2 of this Example is not a single membrane shown in FIG. 1, but may be a composite membrane comprising a main membrane 6 having the same function as that of the selective gas permeable membrane 2 and an auxiliary membrane 7 for elevating the strength as shown in FIG. 3.

When the detection of the hydrogen gas in the same mixed gases was then performed employing the sensor shown in FIG. 1, the existence of 100 ppm of the hydrogen gas was indicated at the detection side after 46 seconds.

What is claimed is:

1. A gas sensor comprising a membrane for gas sensing which comprises a selective gas permeable membrane and a reaction layer attached thereto; and a counter electrode separated from the reaction layer of the membrane across an electrolyte; the reaction layer having the function of an electrode and comprising fine hydrophilic portions and fine hydrophobic portions.

2. A gas sensor as claimed in claim 1, wherein the selective gas permeable membrane comprises a main membrane for selective gas permeation and an auxiliary layer for reinforcement in contact with the reaction layer.

3. A gas sensor as claimed in claim 1, wherein electrode materials are contained in the reaction layer.

* * * * *